(12) United States Patent
Singh

(10) Patent No.: US 9,549,924 B2
(45) Date of Patent: *Jan. 24, 2017

(54) USE OF BUPRENORPHINE DIMER IN THE TREATMENT OF PERIPHERAL NEUROPATHIC PAIN

(71) Applicant: OrphoMed Inc., Mill Valley, CA (US)

(72) Inventor: Nikhilesh Nihala Singh, Mill Valley, CA (US)

(73) Assignee: ORPHOMED, INC., Mill Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/922,373

(22) Filed: Oct. 26, 2015

(65) Prior Publication Data

US 2016/0038481 A1 Feb. 11, 2016

Related U.S. Application Data

(63) Continuation-in-part of application No. 14/697,155, filed on Apr. 27, 2015, now Pat. No. 9,309,256, which is a continuation-in-part of application No. 14/697,174, filed on Apr. 27, 2015, now Pat. No. 9,321,780.

(60) Provisional application No. 61/985,207, filed on Apr. 28, 2014, provisional application No. 62/101,768, filed on Jan. 9, 2015, provisional application No. 62/176,883, filed on Jan. 9, 2015.

(51) Int. Cl.

| | |
|---|---|
| A61K 31/485 | (2006.01) |
| A61K 9/00 | (2006.01) |
| A61K 31/137 | (2006.01) |
| A61K 31/167 | (2006.01) |
| C07C 217/64 | (2006.01) |
| C07C 217/70 | (2006.01) |
| C07C 233/25 | (2006.01) |
| C07D 489/02 | (2006.01) |
| C07D 489/08 | (2006.01) |
| C07D 489/12 | (2006.01) |
| C07D 519/00 | (2006.01) |

(52) U.S. Cl.
CPC .......... *A61K 31/485* (2013.01); *A61K 9/0019* (2013.01); *A61K 31/137* (2013.01); *A61K 31/167* (2013.01); *C07C 217/64* (2013.01); *C07C 217/70* (2013.01); *C07C 233/25* (2013.01); *C07D 489/02* (2013.01); *C07D 489/08* (2013.01); *C07D 489/12* (2013.01); *C07D 519/00* (2013.01); *C07C 2101/14* (2013.01)

(58) Field of Classification Search
USPC ........................................................ 514/279
See application file for complete search history.

(56) References Cited

U.S. PATENT DOCUMENTS

| | | | |
|---|---|---|---|
| 3,896,235 A | 7/1975 | Harfenist | |
| 5,716,631 A | 2/1998 | Drizen et al. | |
| 7,056,500 B2 | 6/2006 | Bentley et al. | |
| 7,084,150 B2 | 8/2006 | Boer et al. | |
| 7,759,358 B2* | 7/2010 | Crooks ................. | A61K 31/44 514/282 |
| 8,063,059 B2 | 11/2011 | Herman | |
| 8,097,239 B2 | 1/2012 | Johnsson et al. | |
| 8,183,376 B2 | 5/2012 | Cheng et al. | |
| 8,461,171 B2 | 6/2013 | Holaday et al. | |
| 8,617,530 B2 | 12/2013 | Roberts et al. | |
| 8,921,387 B2 | 12/2014 | Norton et al. | |
| 8,962,647 B1 | 2/2015 | Guo et al. | |
| 9,044,450 B2 | 6/2015 | Luk et al. | |
| 9,132,144 B2 | 9/2015 | Chen et al. | |
| 9,309,256 B2 | 4/2016 | Singh | |
| 9,321,780 B2 | 4/2016 | Singh | |
| 2005/0075361 A1 | 4/2005 | Wang | |
| 2010/0068786 A1 | 3/2010 | Chmielewski et al. | |
| 2011/0160239 A1 | 6/2011 | Brodbeck et al. | |
| 2011/0245287 A1 | 10/2011 | Holaday et al. | |

FOREIGN PATENT DOCUMENTS

| | | |
|---|---|---|
| EP | 1 422 230 A1 | 5/2004 |
| WO | 03/032990 A2 | 4/2003 |
| WO | 2004/103317 A2 | 12/2004 |
| WO | 2013/123824 A1 | 8/2013 |
| WO | 2015/168014 A1 | 11/2015 |
| WO | 2015/168031 A1 | 11/2015 |

OTHER PUBLICATIONS

International Search Report and Written Opinion corresponding to PCT/US2015/027820 mailed Jul. 3, 2015 (14 pages).
International Search Report and Written Opinion corresponding to PCT/US2015/027781 mailed Sep. 9, 2015 (19 pages).
Bagnol, D. et al., "Cellular Localization and Distribution of the Cloned Mu and Kappa Opioid Receptors in Rat Gastrointestinal Tract," *Neuroscience* (Nov. 1, 1997); 81(2):579-591.
Becker, Gerhild, M.D. et al., "Peripherally Acting Opioid Antagonists in the Treatment of Opiate-Related Constipation: A Systematic Review," *Journal of Pain and Symptom Management* (Nov. 2007; accepted for publication Dec. 21, 2006); 34(5): 547-.
Berge, Stephen M. et al., "Pharmaceutical Salts," *Journal of Pharmaceutical Sciences* (Jan. 1, 1977); 66(1): 1-19.
Bhounsule, Sushama A. et al., "Gastrointestinal actions of buprenorphine: are different receptors involved?" *European Journal of Pharmacology* (Dec. 1, 1996); 361(2-3):253-256.

(Continued)

*Primary Examiner* — Charanjit Aulakh
(74) *Attorney, Agent, or Firm* — Mintz, Levin, Cohn, Ferris, Glovsky and Popeo, P.C.

(57) ABSTRACT

The present invention provides method and compositions for the treatment of peripheral neuropathic pain by administering to a patient a therapeutically effective amount of a buprenorphine dimer compound, wherein the two buprenorphine portions are linked via an ethylene spacer, and wherein the spacer is bonded to the two opioid molecules via an ether bond. Preferably, the active agent is provided in the form of an injectable depot.

9 Claims, 7 Drawing Sheets

(56) References Cited

OTHER PUBLICATIONS

Camilleri, M. "Current and future pharmacological treatments for diarrhea-predominant irritable bowel syndrome," *Expert Opinion on Pharmacotherapy* (Jun. 1, 2013); 14(9):1151-1160.
Cuer, J. C. et al., "Effects of Buprenorphine on Motor Activity of the Sphincter of Oddi in Man," *Eur J Clin Pharmacol* (Feb. 1, 1989); 36:203-204.
Feinberg, Andrew et al., "The opiate receptor: A model explaining structure-activity relationships of opiate agonists and antagonists," *Proc. Natl. Acad. Sci. USA* (Nov. 1, 1976); 73(11):4215-4219.
Haddad, Nizar et al., "Synthesis of a salbutamol dimer," *Tetrahedron Letters* (Feb. 11, 2002); 43(7):1135-1137.
Holzer, Peter, "New approaches to the treatment of opioid-induced constipation," *Eur Rev Med Pharmacolo Sci.* (Aug. 1, 2008); 12(01): 119-127.
Koppert, Wolfgang et al., "Different profiles of buprenorphine-induced analgesia and antihyperalgesia in a human pain model," *Pain* (Jun. 5, 2005); 118:15-22.
Kumar, Ramesh et al., "Synthesis and evaluation of acetaminophen derivatives as analgesic, antipyretic and anti-inflammatory agents," *Der Pharma Chemica* (Mar. 6, 2013); 5(3):73-78.
Richards, Ryan, "Opioid Analgesics" (www.faculty.smu.edu): "A free phenol group is crucial for analgesic activity." (Oct. 29, 2015); 51 pages.
Rumack, Barry H., M.D. et al., "Acetaminophen Poisoning and Toxicity," *Pediatrics* (Jun. 1, 1975); 55:871-876.
Startiz, M. et al., "Effect of modern analgesic drugs (Tramadol, pentazocine, and buprenorphine) on the bile duct sphincter in man," *Gut* (May 1, 1986); 27:567-569.
Thorpe, David H., M.D., "Opiate Structure and Activity—A Guide to Understanding the Receptor," *Anesth Analg.* (Feb. 1, 1984); 63:143-151.
Zakko, S. et al., "Randomised clinical trial: the clinical effects of a novel neurokinin receptor antagonist, DNK333, in women with diarrhea-predominant irritable bowel syndrome," *Alimentary Pharmacology & Therapeutics* (Apr. 20, 2011); 33(12):1311-1321.
Dunee (posted by) Mar. 6, 2012, "Difference Between Ester and Ether," http://www.differencebetween.com/difference-between-ester-and-vs-ether/: (downloaded Jun. 9, 2016); 5 pages.
Huttunen, Kristiina et al, Prodrugs—from Serendipity to Rational Design, *Pharmacological Reviews* (2011) 63:750-771; (downloaded from pharmrev.aspetjournals.org on Apr. 25, 2016).
Parang, Keykavous et al., Novel Approaches for Designing 5'-O'Ester Prodrugs of 3'-Azido-2'3'-Dideoxythymidine (AZT), *Chapman University; Chapman University Digital Commons; Pharmacy Faculty Articles and Research* (2000); http://digitalcommons.chapman.edu/cgi/viewcontent.cgi?article=1105&context=pharmacy_articles (downloaded Jun. 2, 2016).

* cited by examiner

Stability of the buprenorphine dimer when exposed to CYP enzymes in the presence and absence of a cofactor Stability of the buprenorphine dimer to aqueous conditions, as well as acidic and basic condition, each at room temperature and at 140°F for the indicated period of time.

Results of buprenorphine dimer receptor binding experiments – µ receptor

Results of buprenorphine dimer receptor binding experiments – κ receptor

μ agonist functional assay results for the buprenorphine dimer

µ antagonist functional assay results for the buprenorphine dimer

Anti-hyperalgesia for the buprenorphine dimer

USE OF BUPRENORPHINE DIMER IN THE TREATMENT OF PERIPHERAL NEUROPATHIC PAIN

CROSS-REFERENCES TO RELATED APPLICATIONS

This application is a continuation-in-part of U.S. application Ser. No. 14/697,155 filed Apr. 27, 2015, which application claims the benefit of priority under 35 U.S.C. §119(e) of U.S. Provisional Application No. 61/985,207 filed Apr. 28, 2014; U.S. Provisional Application No. 62/101,768 filed Jan. 9, 2015; and U.S. Provisional Application No. 62/176,883 filed Jan. 9, 2015; this application is a continuation-in-part of U.S. application Ser. No. 14/697,174 filed Apr. 27, 2015, which application claims the benefit of priority under 35 U.S.C. §119(e) of U.S. Provisional Application No. 61/985,207 filed Apr. 28, 2014; U.S. Provisional Application No. 62/101,768 filed Jan. 9, 2015; and U.S. Provisional Application No. 62/176,883 filed Jan. 9, 2015, each of which is herein incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Peripheral Neuropathic Pain

Chronic pain may be divided into two major categories: "nociceptive" pain (caused by inflamed or damaged tissue that activates specialized pain sensors called nociceptors), and "neuropathic" pain (caused by damage to or malfunction of the nervous system). Neuropathic pain may either be "peripheral", which originates in the peripheral nervous system, or "central", which originates in the brain or spinal cord.

Peripheral neuropathic pain is a chronic condition that is very common in clinical practice. Peripheral neuropathic pain can have many underlying causes, including diabetes, alcoholism, vitamin deficiencies, injury, toxic reactions to prescribed drugs, infectious diseases, malignancies, etc.

Several mechanisms contribute to the development and severity of neuropathic pain, which are very different from the mechanisms that cause nociceptive pain. As a result of nerve damage, several pathologic changes may occur including:

Impulse generation within the damaged nerve fiber
    Nerve fiber to nerve fiber interactions
    Failure of the normal nerve fiber inhibitory mechanisms
    Plasticity—degeneration and regeneration of the injured nerve fibers that results in altered conductivity The pain associated with peripheral neuropathy may be severe and, unlike most pain that sufferers have previously experienced, it is characterized by allodynia (pain response from stimuli that do not normally provoke pain), hyperalgesia and in some cases, sensory loss. The pain is often described as "burning, stabbing, raw or sickening". It can be constant or paroxysmal and with or without sensory impairment. The type and severity of pain or sensory loss depends on the underlying cause of the neuropathy. In chronic forms of neuropathic pain, symptoms begin subtly and progress slowly. Some people may have periods of relief followed by relapse. Others may reach a plateau stage where symptoms stay the same for many months or years. Many chronic neuropathies worsen over time. For the majority of patients with neuropathic pain, the pain will persist for life. Comorbidities such as depression, poor quality of life and employment and domestic issues are very common.

More than 100 types of peripheral neuropathy have been identified, each with its own symptoms and prognosis. In general, peripheral neuropathies are classified according to the type of damage to the nerves. Some forms of neuropathy involve damage to only one nerve and are called mononeuropathies. More frequently, however, multiple nerves are affected, called polyneuropathy.

Common types of peripheral neuropathic pain are depicted in Table 1:

TABLE 1

Common Types of Peripheral Neuropathic Pain

Acute and chronic inflammatory demyelinating polyradiculoneuropathy
Alcoholic polyneuropathy
Chemotherapy-induced polyneuropathy
Complex regional pain syndrome
Entrapment neuropathies (eg, carpal tunnel syndrome)
HIV sensory neuropathy Iatrogenic neuralgias (eg, postmastectomy pain or post-thoracotomy pain)
Idiopathic sensory neuropathy
Nerve compression or infiltration by tumor
Nutritional deficiency-related neuropathies
Painful diabetic neuropathy
Phantom limb pain
Post-herpetic neuralgia
Post-radiation plexopathy
Radiculopathy (cervical, thoracic, or lumbosacral)
Toxic exposure-related neuropathies
Tic douloureux (trigeminal neuralgia)
Post-traumatic neuralgia

Treatment of Neuropathic Pain with Opioid Analgesics

Many different drugs with a variety of mechanisms of action have been used to treat neuropathic pain, among them the opioids oxycodone and tramadol (Ultram™). None have had complete success and all have significant associated adverse events. A common adverse event of opioid analgesics is sedation, related to the central nervous system effects of these drugs. In many patients, especially elderly patients, treatment with opioid analgesics may result in problems of impairment and mobility, which may increase the risk of hip fractures. All patients that use opioid analgesics on a chronic basis will develop physical dependence and stopping the medication for any reason would require them to be under close medical care.

Buprenorphine, a partial opioid mu agonist and full opioid delta and kappa antagonist, has been extensively studied in patients with neuropathic pain. As an analgesic, it is approximately 30 times more potent than morphine. Buprenorphine has been shown to not only have an analgesic effect but also to have significant antihyperalgesic (antihypersensitivity) properties. Hyperalgesia is a component of neuropathic pain. The major drawback of prescribing buprenorphine for this purpose, however, is that as an opioid mu receptor agonist, it has significant addictive properties and would not be suited for safe long-term use.

Peripheral neuropathic pain is by nature local, affecting one or more areas of the body and the doses required to treat the local condition by intravenous delivery would seem to rule out buprenorphine itself for this purpose. For the treatment of opioid dependence, it is true that buprenorphine has previously been formulated for subcutaneous long-acting depot injection. (See U.S. Pat. Nos. 8,921,387 and 8,975,270). A buprenorphine depot formulation for the treatment of peripheral neuropathic pain, however, would appear to offer irreconcilable choices between, on the one hand, sufficient dose to treat local pain, and on the other concerns about the agent's access to the central nervous system and it's significant consequences.

There has accordingly been a long-felt need for a treatment for peripheral neuropathic pain that offers analgesic properties akin to those of buprenorphine but without the adverse effects expected to accrue from use of the opioid for that purpose.

BRIEF SUMMARY OF THE INVENTION

We have now synthesized as a new chemical entity a dimer comprising two buprenorphine moieties conjugated to each other by O-alkylation through their phenolic groups to yield the structure of Formula (I):

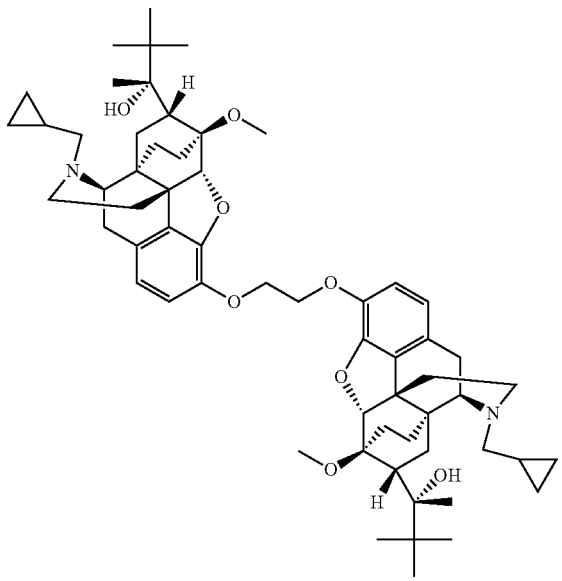

Formula (I)

In Formula (I), the compound is:
2,2'-((4aR,4a'R,6S,6'S,7S,7'S,12bR,12b'R)9,9'-(ethane-1,2-diylbis(oxy))bis(3-(cyclopropylmethyl)-7-methoxy-1,2,3,4,5,6,7,7a-octahydro-4a,7-ethano-4,12-methanobenzofuro[3,2-e]isoquinoline-9,6-diyl))bis(3,3-dimethylbutan-2-ol) (Compound 1, or buprenorphine dimer). Its molecular weight is 961.28.

The dimer has been shown to retain the receptor affinity and pharmacologic characteristics of the parent compound, buprenorphine. It maintains potent binding affinities for the mu, delta and kappa receptors. The molecular weight of the dimer is greater than 1000 daltons, which prevents it from being absorbed and entering the central nervous system. A study of the buprenorphine dimer administered intravenously to mice demonstrated rapid elimination. Mice showed no evidence of CNS activity in that there was no change in behavior. More recently, in a rodent study to determine the antihyperalgesic effects of the dimer, significant antihyperalgesic activity was demonstrated, while no evidence of CNS activity was evident, in that there was no change in behavior of test mice.

In summary, the dimer when administered intramuscularly or subcutaneously, either by immediate-acting formulation or by long-acting depot formulation, based on laboratory data, is expected to have potent systemic analgesic and antihyperalgesic properties excluding the central nervous system. The dimer, because of its strong covalent ether ethylene glycol linker, is stable and does not undergo metabolism. No metabolism to buprenorphine has been detected in experiments conducted to date. The potent peripherally acting (non-CNS) drug behavior makes this drug very suitable for the treatment of painful peripheral neuropathies. Its potent mu opioid agonist and kappa antagonist effects and lack of CNS absorption, result in it being unique among analgesic agents.

In one embodiment, the invention provides for the use of the compound of Formula I or a pharmaceutically acceptable salt or solvate thereof in the treatment of peripheral neuropathic pain by subcutaneous or intramuscular administration of a therapeutically effective dose. Injection may be subcutaneous or intramuscular in solution for initial treatment of acute pain. Preferably, however, the invention provides a method for the treatment of peripheral neuropathic pain by injecting a depot formulation of a therapeutically effective amount of the dimer for slow release over time. Most preferably, the compound is provided in a slow release formulation for subcutaneous injection.

In another embodiment the invention provides pharmaceutical compositions for use in the treatment of peripheral neuropathic pain.

The manner in which these and other objects of the invention are achieved will be apparent from the attached Figures and the detailed description of the invention that follows.

Figure 1:
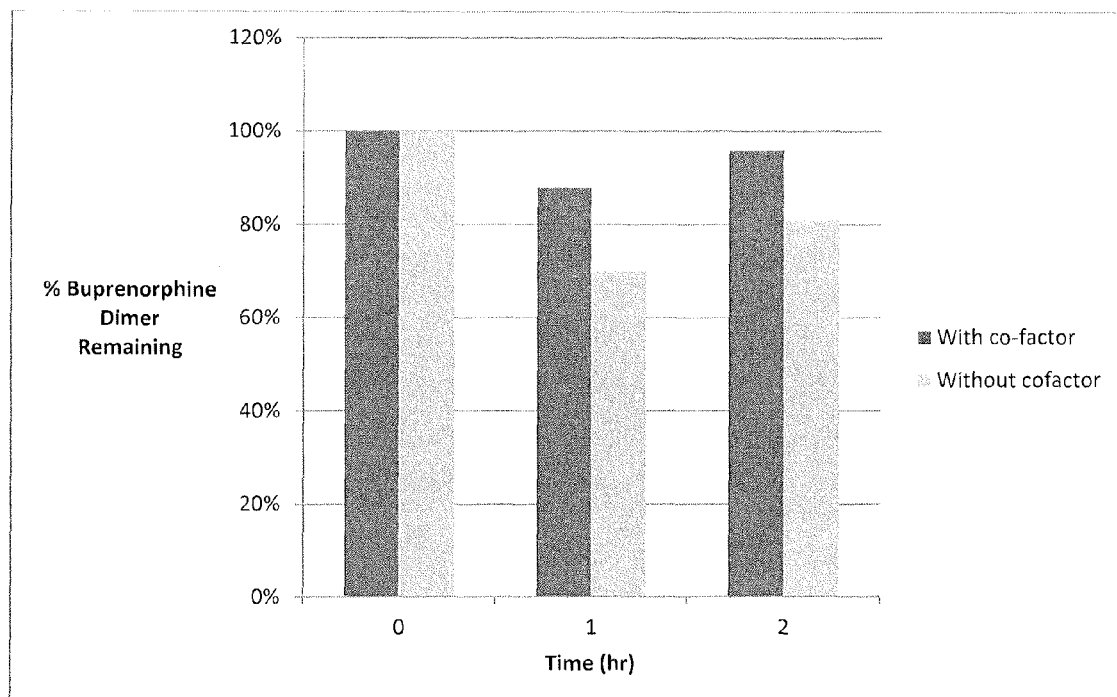
FIG. 1 provides a bar chart illustrating the stability of buprenorphine dimer when exposed to CYP enzymes in the presence and absence of a co-factor.

In the case of work underlying each Figure, the compound was employed in the form of its hydrochloride salt.

DETAILED DESCRIPTION

Conventional wisdom has been that derivatization of the phenolic groups of morphinones by replacing hydrogen with a less hydrophilic substituent would substantially reduce the opioid potency of the resulting opioid. See Feinberg Andrew F, et al. Proc Natl Acad Sci. USA Volume 73 no 11 p 4215-4219 (1976). According to R. Richards, Opioid Analgesics (www.faculty.smu.edu): "A free phenol group is crucial for analgesic activity." In Anesth Analg 1984; 63; 143-51 at 145 et seq, D. H. Thorpe says "Another portion of the morphine molecule thought to interact with the receptor is the phenol moiety. Muzzling the free hydroxyl group with a methyl group reduces potency more than ten-fold . . . ." The author goes on to cite other studies showing that larger alkyl groups have an even more deleterious effect, concluding that "bulkiness . . . is responsible for the decreased binding effect." See also U.S. Pat. Nos. 8,183,376 and 8,461,171.

Despite the steric hindrance one might have expected from linking two such bulky molecules, the buprenorphine dimer surprisingly retains the pharmacologic receptor activity of the parent opioid, including the anti-hyperalgesia activity thereof. By reason of its size and lipophilicity it is less likely to penetrate the blood brain barrier. Indeed, when administered to mice no evidence of CNS activity was observed. The dimer compound of the invention is therefore indicated for the treatment of peripheral neuropathic pain.

As noted above, the present invention employs a dimeric form of buprenorphine where the two buprenorphine molecules are linked via a covalent bond between the phenolic (3-hydroxyl) functional group of each buprenorphine molecule and an ethylene linker. The ethylene linker serves as a spacer between the two buprenorphine molecules and is thought to prevent the two bulky buprenorphine molecules from adopting an enclosed ring conformation via either a covalent, ionic or Van der Waal interaction between other functional groups on the molecules.

Surprisingly, when two drug molecules are conjugated to each other via an ethylene spacer, wherein the spacer is attached to the phenyl ring of each drug molecule via an ether bond, the resulting dimer is found to be chemically and metabolically stable, and is not de-conjugated when exposed to metabolic enzymes. Additionally, surprisingly and unexpectedly, the dimer retains the pharmacological activity of the parent compound.

In contrast to buprenorphine, the buprenorphine dimer, prepared as described herein retains the opioid μ and κ activity not only in form but also direction, viz. neither receptor affinity nor activity is compromised. Additionally, the buprenorphine dimer described herein is relatively stable to metabolism in in vivo and in vitro experiments. The buprenorphine dimer appears metabolically stable, even after exposure to the liver of live mice, following intravenous injection.

Still further, it was also found that the buprenorphine dimer retained, selectively, only the μ and the κ functions of buprenorphine, but was significantly stripped of its δ function. Stated differently, the buprenorphine dimer, unlike buprenorphine, is a selective μ and κ active molecule without significant δ activity.

DEFINITIONS

When describing the compounds, compositions, methods and processes of this invention, the following terms have the following meanings, unless otherwise indicated.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Numerical quantities given herein are approximate unless stated otherwise, meaning that the term "about" or "approximately" can be inferred when not expressly stated.

The term "administering," "administration" and derivatives thereof refers to the methods that may be used to enable delivery of agents or compositions to the desired site of biological action.

The term "chronic pain" refers to pain persisting for an extended period of time, for example, greater than three to 6 months, although the characteristic signs of pain can occur earlier or later than this period. Chronic pain may be mild, excruciating, episodic, or continuous.

The term "composition" as used herein is intended to encompass a product comprising the specified ingredients in the specified amounts, as well as any product which results, directly or indirectly, from combination of the specified ingredients in the specified amounts.

The term "therapeutically effective amount" refers to that amount of the therapeutic agent sufficient to ameliorate the targeted condition or symptoms.

The term "treating," "treatment" and derivatives thereof to refers to the treating or treatment of a disease or medical condition (such as pain) in a patient, such as a mammal (particularly a human or an animal) which includes: ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient.

The term "pharmaceutically acceptable" carrier, diluent, or excipient is a carrier, diluent, or excipient compatible with the other ingredients of the formulation and not deleterious to the recipient thereof.

The term "subject," "individual" or "patient" refers to an animal such as a mammal, including, but not limited to, primates (e.g., humans), cows, sheep, goats, horses, dogs, cats, rabbits, rats, mice and the like.

Synthesis of the Buprenorphine Dimer

Synthesis of the buprenorphine dimer provided herein can proceed by a general O-alkylation reaction in an organic solvent (such as, e.g., acetonitrile, DMF, DMSO, NMP, DCM, THF, 1,4-Dioxane) in the presence of inorganic base (such as, e.g., sodium hydroxide, potassium carbonate, sodium carbonate, cesium carbonate, potassium bicarbonate and sodium bicarbonate) or organic base (such as, e.g., triethylamine, Hunig's base, DMAP and pyridine) at room temperature or elevated temperature. Suitable alkylating agents that can be used include diiodo, dibromo, dichloro, ditosylate, dimesylate and ditriflate reagents (e.g., 1,2-ethylene ditosylate, 1,2-ethylene dimesylate). The free base or a salt of buprenorphine can be employed as a starting material in the synthesis.

Pharmaceutical Compositions of the
Dimer—General

In certain embodiments, provided herein are compositions comprising a buprenorphine dimer of Formula A pharmaceutical composition can further comprise a pharmaceutically acceptable carrier. Illustrative pharmaceutically acceptable carriers and formulations are described below. Such pharmaceutical compositions can be used to treat peripheral neuropathic pain.

As will be appreciated, a pharmaceutically acceptable salt of a dimer may be used instead of or in addition to a dimer in any or all of the compositions and methods of treating discussed herein. Thus, in specific embodiments, a pharmaceutically acceptable salt of the dimer (i.e., any pharmaceutically acceptable salt of any of the dimers) is used in the methods of the invention. These salts can be prepared, for example, in situ during the final isolation and purification of the compound or by separately reacting the purified compound in its free base form with a suitable organic or inorganic acid and isolating the salt thus formed. In some embodiments, the pharmaceutically acceptable salt of the buprenorphine dimer is prepared using acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, or p-toluenesulfonic acid. For further description of pharmaceutically acceptable salts that can be used in the methods described herein see, for example, S. M. Berge et al., "Pharmaceutical Salts," 1977, J. Pharm. Sci. 66:1-19, which is incorporated herein by reference in its entirety.

The buprenorphine dimer can exist in unsolvated as well as solvated forms with pharmaceutically acceptable solvents such as water, ethanol, and the like. In general, the solvated forms are considered equivalent to the unsolvated forms for the purposes of the present invention. In a specific embodiment, the solvated form of the dimer is a hydrate.

In general, salt formation may improve shelf life of the resultant therapeutic agent. Appropriate salt synthesis can afford products that are crystalline, less prone to oxidation and easy to handle. Various salts can be prepared that would afford stable and crystalline compounds. A few examples are hydrochloric, sulfuric, p-toluenesulfonic, methanesulfonic, malonic, fumaric, and ascorbic acid salts.

Formulation of the Dimer

For parenteral administration by intramuscular or subcutaneous routes, the dimer may be formulated for acute administration or for chronic administration as a depot, long-term injectable or implantable. Injectables may be present in the dosage form as a solution, a dispersion in solution, or as a powder or two components to be mixed prior to use.

Acute Formulations

The most basic acute vehicle for injection comprises saline solution, which is comprised of water for injection (WFI) and 0.9% saline solution. Other suitable aqueous vehicles include Ringer's injection, dextrose solution, dextrose and sodium chloride solution, and Lactated Ringer's Injection. To improve solubility of the drug, nonaqueous water miscible vehicles may be added including ethanol, propylene glycol, polyethylene glycol 300 or 400. Surfactants such as polysorbate 20 or 80, Cremophor EL, Solutol HS 15 and many others may be added to improve solubility. Oils may be used as nonaqueous vehicles, especially corn oil, cottonseed oil, peanut oil, and sesame oil. Other nonaqueous vehicles include ethyl oleate, isopropyl myristate, glycerol monoleate, benzyl benzoate and many others. Antimicrobial agents such as cresol, chlorobutanol, phenylmercuric nitrate, thimerosol, benzalkonium chloride, benzethonium chloride, phenol, methyl p-hydroxybenzoate, propyl p-hydroxybenzoate, benzyl alcohol, and many others may be added alone or in combination. Antioxidants or chelating agents may be added such as sodium bisulfite, thiourea, EDTA, citric acid or citrate buffer, tocopherol or its derivatives, cysteine, methionine, ascorbic acid or mixtures thereof. The above groups of excipients may be added in combination. All of these additives and potential vehicles may also be used for chronic formulations.

Chronic Formulations

Preferably, for the treatment of chronic pain the dimer compound will be delivered in a composition suitable for implantation or injection intramuscularly or, most preferably, by subcutaneous depot injection or implantation, Depots from Oils Long acting formulations may be made by incorporation of the dimer in an oil, as listed above, and its slow release from that oil. Alternatively, a salt with a fatty acid may be prepared to lower the solubility and provide a slow rate of dissolution. Both approaches may be combined.

Long-Term Injectables

1. Phospholipids

A phospholipid depot, as taught in U.S. Pat. No. 9,132,144, may be formed from the dimer in an oil in water emulsion comprised of a phospholipid and an oil. The emulsion is formed by homogenization and then made into a single phase by microfluidizing. A buffer may be added to maintain the pH. A dry paste is then formed by lyophilization, and ethanol and or isopropanol is added to the paste as 1 to 25% of the formulation to modify the viscosity so that it may be injected through a size 22 needle. Alternatively, N-methyl pyrrolidone (NMP) may be added to modify viscosity. The clear gel depot formed is sterilized. Antioxidants and/or chelating agents such as EDTA, citric acid or citrate buffer, tocopherol or its derivatives, cysteine, methionine, ascorbic acid, or mixtures thereof may optionally be added. Examples of oils are vegetable oils such as sunflower oil, corn oil, olive oil, peanut oil, cottonseed oil, soybean oil, sesame oil, and the like, or animal oils such as fish oil, or synthetic oils such as glycerol monoleate, propylene glycol monolaurate or monocaprylate, or CAPMUL™. A list of phospholipids that may be used may be found in the referenced patent.

A liquid crystalline injectable gel may also be formed by the use of a phospholipid, glycerol dioleate, and ethanol or NMP (U.S. Pat. No. 8,097,239).

2. Poloxamer Gels

Thermoreversible gels may be made using Poloxamer™, particularly Poloxamer 407, in about 15 to 25% solutions comprised also of the dimer and physiological saline (0.9% sodium chloride solution). These solutions at room temperature may be passed through a size 22 needle and at body temperature form a gel from which the drug may be slowly released over a period of days or longer. Additional polymer such as 2% hypromellose, or phospholipid such as 1 to 4% lecithin, may be added. Buffer such as citrate, phosphate or acetate buffer at pH 4 to 7, and preferably pH 5 to 6 may be added.

3. Other Viscous Gels

Other viscous injectable gels may be formed by polymers or copolymers of lactic (PLA) or lactic and glycolic acids (PLGA) dissolved in N-methyl pyrrolidone (NMP), ethyl benzoate, or benzyl benzoate, as disclosed in U.S. Pat. No.

9,044,450. Another viscous gel that may form in situ after injection into the body is SABER™ gel from Durect Corporation comprising sucrose acetate isobutyrate. For example, about 63% NMP has been used with D,L polylactic acid PLA) to produce a biodegradable gel in the body after injection (Atrigel™).

4. Microsphere Injectables and Implants

Both microsphere injectables and implants are made from biodegradable polymers that degrade in the body to release drug. These include PLA, PLGA or combinations, polyanhydrides, poly ortho-esters, and others. Drug matrices may be prepared from hyaluronic acid (U.S. Pat. No. 5,716,631). Examples are microspheres containing naltrexone (337 mg/1 g PLGA microspheres, Vivitrol). This is supplied as a kit with the microspheres needing to be suspended in the separate diluent consisting of polysorbate 80, sodium croscarmellose, saline, and WFI. Another depot, Leuprolide, also supplies lyophilized microspheres with drug to be resuspended in diluent comprising polysorbate 80, sodium croscarmellose, saline, D-mannitol, glacial acetic acid to control pH, and WFI.

5. Implants

PLA or PLGA may be extruded with drug to form an implant as in U.S. Pat. No. 6,620,422.

Implants may also be made of polymers that are not biodegradable. For example ethylene vinyl acetate (EVA) implants loaded with drug may extruded, implanted in the doctor's office with a trocar and then surgically removed when desired.

6. ATRIGEL™

Particularly suited for the delivery of the dimer in chronic treatment is the ATRIGEL™ product available from QLT-USA, Fort Collins, Colo. ATRIGEL is the thermoplastic polymer poly(lactide-co-glycolide) (PLG), the thermoplastic polymer poly(lactide-co-glycolide extended with 1,6-hexane diol) (PLG), or PLGH in the organic solvent N-methyl-2-pyrrolidone. Buprenorphine itself is formulated in ATRIGEL for the treatment of opioid dependency in U.S. Pat. No. 8,921,387, whose disclosure is incorporated herein by reference.

Methods of Treatment

A "therapeutically effective amount" refers to that amount of the therapeutic agent, which yields an appreciable and beneficial effect on the treated indication. In certain embodiments, the patient is a mammal. In more specific embodiments, the patient is a human. In certain specific embodiments, the patient may be a domesticated mammal such as a dog, a cat, or a horse.

The dose of the buprenorphine dimer provided herein to be administered to a patient is rather widely variable and can be subject to the judgment of a health-care practitioner. Dosage may be properly varied depending on the age, body weight and medical condition of the subject and the type of administration. In any given case, the amount of the dimer provided herein administered will depend on such factors as the solubility of the active component, the formulation used and the route of administration.

For single use, acute or immediate release injection, the preferred dose of dimer may be between at least 0.3 and not more than 25 mg, more preferably between at least 1 mg and not more than 20 mg, and still more preferably between at least 2.5 mg and not more than 15 mg. The single use dose can be available as a solution, suspension or as a powder to be reconstituted with an injectable diluent.

For weekly depot injection, the preferred dose of dimer may be between about 5 mg and about 120 mg, more preferably between about 10 mg and 100 mg, and still more preferably between about 15 mg and about 80 mg. The weekly depot can be available as an injectable solution, gel, suspension or as a powder to be reconstituted with an injectable diluent. Preferably the depot is injectable through a syringe needle gauge 21.

For monthly or 30-day depot injection, the dose of dimer may be about 25 mg to about 200 mg, preferably about 30 mg to about 150 mg, and still more preferably about 40 mg and about 120 mg. The weekly depot can be available as an injectable solution, gel, suspension or as a powder to be reconstituted with an injectable diluent. Preferably the depot is injectable through a syringe needle gauge 21.

In the foregoing, all weights are expressed as dimer base.

EXAMPLES

The following examples are offered to illustrate, but not to limit the claimed invention.

Example 1

Synthesis

Buprenorphine dimer was synthesized as shown below.

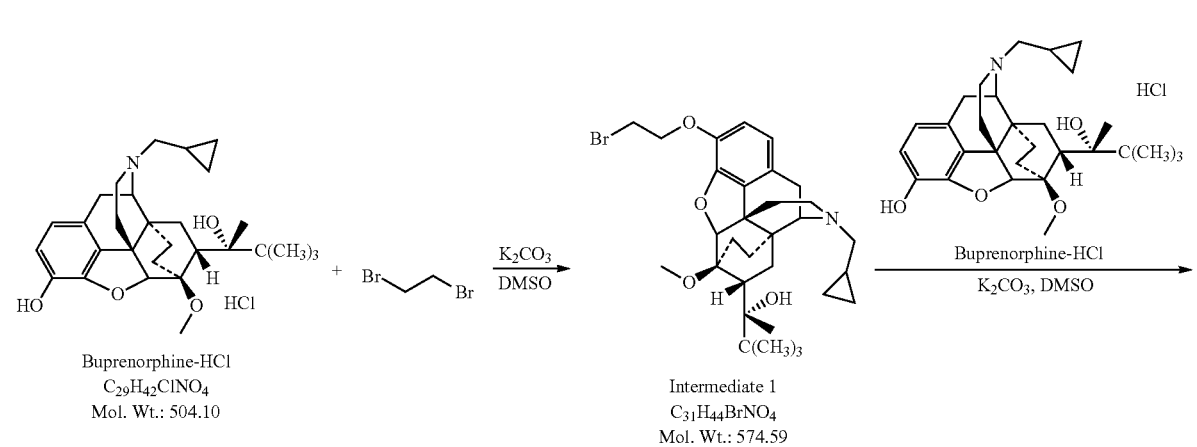

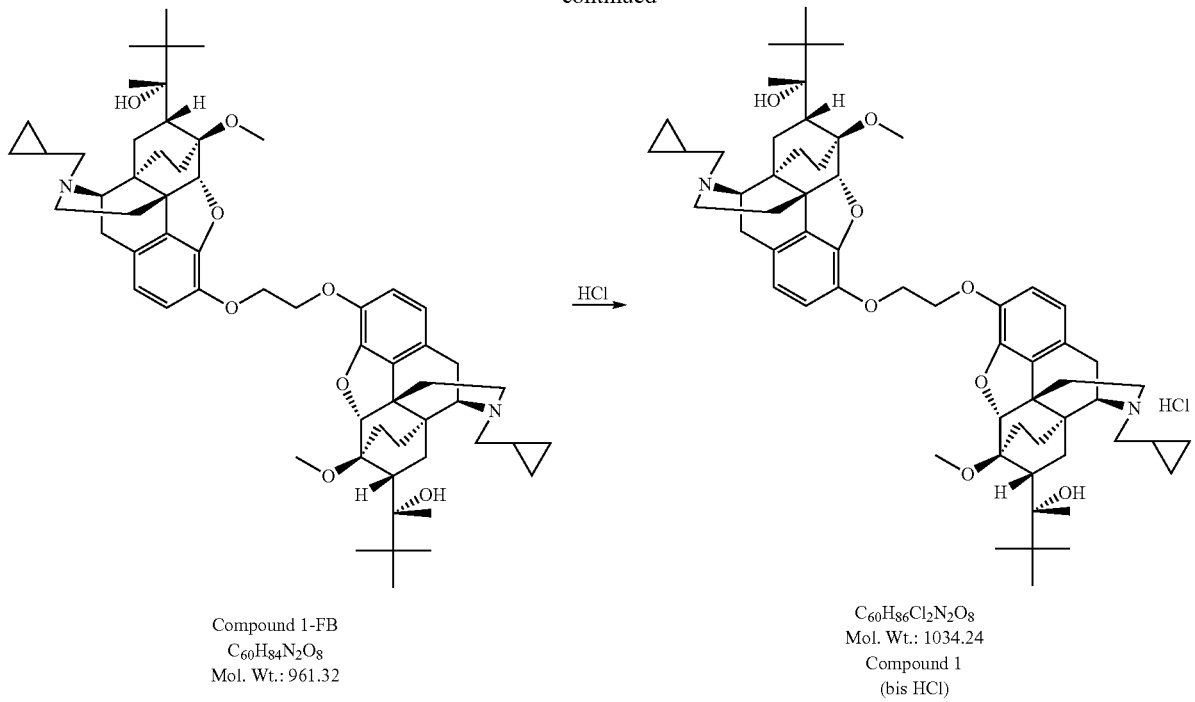

Compound 1-FB
$C_{60}H_{84}N_2O_8$
Mol. Wt.: 961.32

$C_{60}H_{86}Cl_2N_2O_8$
Mol. Wt.: 1034.24
Compound 1
(bis HCl)

Buprenorphine HCl-salt (5.0 g, 10.68 mmol, 1 equiv) and potassium carbonate (42.73 mmol, 4 equiv) were charged in a 3-neck round bottom flask followed by anhydrous DMSO (50 ml, 10 vol). The mixture was heated to 60° C. and 1,2-dibromoethane (9.2 mL, 106.8 mmol, 10 equiv) was added slowly. The reaction mixture was stirred at 60° C. for 16 h then cooled to room temperature, diluted with water and extracted with dichloromethane. The combined organic portions were washed with brine, dried (anhydrous Na2SO4), filtered and concentrated under reduced pressure to afford a viscous liquid. The crude product was purified by silica gel chromatography using 0-5% MeOH/DCM to afford 4.2 g (69%) Intermediate 1 as off-white foamy solid.

Buprenorphine HCl-salt (1.74 g, 3.72 mmol) and potassium carbonate (2.0 g, 14.87 mmol, 4 equiv) were charged in a 3-neck round bottom flask followed by anhydrous DMSO (10 mL). The mixture was heated to 60° C. and Intermediate 1 (3 g, 5.22 mmol, 1.4 equiv) dissolved in 7 mL of anhydrous DMSO was added dropwise over a period of 2 h. The reaction mixture was stirred at 60° C. for 16 h then cooled to room temperature, diluted with water and extracted with dichloromethane. The organic layer was washed with brine, dried (anh. Na2SO4), filtered and concentrated under reduced pressure to afford a viscous liquid. The crude product was purified by silica gel chromatography using 0-5% MeOH/DCM to afford Buprenorphine dimer-FB (free base) as foamy solid (2.8 g, 77%).

5.5 g (5.7 mmol) of bi-conjugate (buprenorphine dimer-FB) was dissolved in 50 mL of ethyl acetate at room temperature under nitrogen. 3.43 mL (6.9 mmol, 1.2 equiv) of 2N HCl in ether was added drop-wise at room temperature. The reaction mixture was stirred at room temperature for additional hour and filtered to obtain a solid. The solid was further washed with 100 ml of ethyl acetate and dried under vacuum to afford buprenorphine dimer (bis HCl salt) as white solid (5.8 g, 98%). 1H NMR (300 MHz, DMSO-d6): δ 9.75 (br, 2H), 6.88 (d, J=9.2 Hz, 2H), 6.67 (d, J=9.2 Hz, 2H), 4.66 (s, 2H), 4.23-4.42 (m, 4H), 3.84-3.92 (m, 2H), 3.40 (s, 6H), 3.21-3.35 (m, 5H), 2.98-3.20 (m, 7H), 2.64-2.85 (m, 4H), 2.12-2.26 (m, 4H), 1.72-1.94 (m, 4H), 1.38-1.52 (m, 4H), 1.26 (s, 6H), 0.99 (s, 20H), 0.48-0.76 (m, 10H), 0.32-0.42 (m, 4H); MS: m/z 962 (M+1)+

Example 2

Assays

1. In Vitro Assay: Metabolic Stability of Buprenorphine Dimer

Incubations of the dimer (e.g., 1 μM) with human liver microsomes (e.g., 1 mg protein/mL) was carried out using a Tecan Liquid Handling System (Tecan), or equivalent, at 37±1° C. in 0.2-mL incubation mixtures (final volume) containing potassium phosphate buffer (50 mM, pH 7.4), MgCl2 (3 mM) and EDTA (1 mM, pH 7.4) with and without a cofactor, NADPH-generating system, at the final concentrations indicated in a 96-well plate format. The NADPH-generating system consisted of NADP (1 mM, pH 7.4), glucose-6-phosphate (5 mM, pH 7.4) and glucose-6-phosphate dehydrogenase (1 Unit/mL). The dimer was dissolved in aqueous methanolic solution (methanol 0.5% v/v, or less). Reactions were started typically by addition of the cofactor, and stopped at four designated time points (e.g., up to 120 min) by the addition of an equal volume of stop reagent (e.g., acetonitrile, 0.2 mL containing an internal standard). Zero-time incubations served as 100% value to determine percent loss of substrate. Incubations were carried out in triplicate with an exception for zero-time samples (which were incubated in quadruplicate). Zero-cofactor (no NADPH) incubations were performed at zero-time and the longest time point. The samples were subjected to centrifugation (e.g., 920×g for 10 min at 10° C.) and the supernatant fractions analyzed by LC-MS/MS. Additional incubations were carried out with microsomes in which were replaced with a marker substrate (e.g., dextromethorphan to monitor substrate loss) as positive controls to determine if the test system is metabolically competent.

The above samples were analyzed by LC-MS/MS. Analysis was performed for the samples at each incubation solution. Results were determined by a comparison of peak ratios over the time course of the experiment (typically reported as "% Parent Remaining").

Data were calculated with a LIMS (includes Galileo, Thermo Fisher Scientific Inc. and reporting tool, Crystal Reports, SAP), the spreadsheet computer program Microsoft Excel (Microsoft Corp.) or equivalent. The amount of unchanged parent compound will be estimated (to determine approximate percent substrate remaining in each incubation) based on analyte/internal standard (IS) peak-area ratios using a LIMS, Analyst Instrument Control and Data Processing Software (AB SCIEX), or equivalent.

Results: Results as shown in FIG. 1 indicate that the dimer of buprenorphine was relatively stable in presence of microsomal enzymes for the duration of the assay. The microsomal enzymes are typically responsible for metabolism of drugs such as buprenorphine. The dimer was stable in presence of the microsomes, with or without the co-factor. The assay was terminated at 2 hours as enzymes are typically not stable beyond 2 hours at incubation temperatures of 37° C.

2. Stability Assay

The goal of the laboratory-based studies was to evaluate the ease with which the patient can retrieve buprenorphine from the dimer and thus compromise its abuse deterrent properties.

These studies facilitate the understanding of the ease with which a potential abuser could cleave the dimer using household chemicals such as baking soda, acid or simple heating in water. Buprenorphine dimer stability was assessed at room temperature in untreated tap water and in presence of acid (1N HCl) or base (5% aqueous sodium bicarbonate). The dimer was relatively stable under those conditions and under these conditions did not appreciably degrade to buprenorphine. See FIG. 2.

Figure 2:
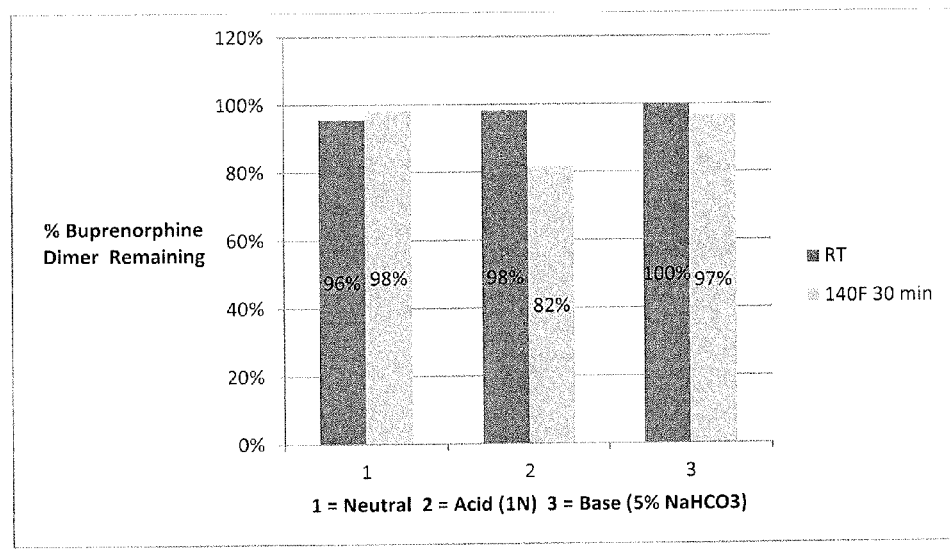
FIG. 2 provides a bar graph showing the stability of buprenorphine dimer to aqueous conditions, as well as acidic and basic condition, each at room temperature and at 140° F. for the indicated period of time.

Results: As shown in FIG. 2, the buprenorphine dimer remained stable and did not degrade to release buprenorphine either at room temperature or elevated temperature under extreme pH conditions even as long as 30 minutes.

These studies also facilitate the understanding of the stability of the dimer in the gastrointestinal tract, which exhibits a gradient pH along its length in both IBS-D and healthy patients. The pH ranges from 1 due to excretion of hydrochloric acid from the parietal cells of the stomach to 8 in the colon. The proximal portion of the gastrointestinal tract is most acidic where the distal end is the least acidic.

Example 3

Receptor Binding Activity

This example illustrates the binding of the buprenorphine dimer provided herein to the following receptors: μ-opioid receptor; κ-opioid receptor; and δ-opioid receptor.

A. Human μ Opioid Receptor Binding Assay

Figure 3:
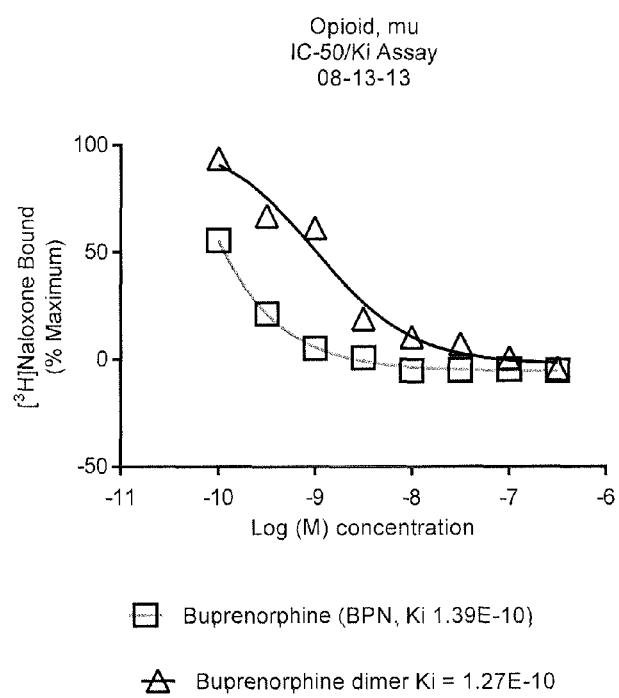
FIG. 3 provides the results of buprenorphine dimer receptor binding experiments—μ receptor.

Membranes from Chinese Hamster Ovary cells expressing the human μ opioid receptor (Perkin Elmer #RBHOMM400UA) were homogenized in assay buffer (50 mM Tris, pH 7.5 with 5 mM MgCl2) using glass tissue grinder, Teflon pestle and Steadfast Stirrer (Fisher Scientific). The concentrates of the membranes were adjusted to 300 μg/mL in assay plate, a 96 well round bottom polypropylene plate. The compound to be tested was solubilized in DMSO (Pierce), 10 mM, then diluted in assay buffer to 3.6 nM. In a second 96 well round bottom polypropylene plate, known as the premix plate, 60 μL of 6× compound was combined with 60 μL of 3.6 nM 3H-Nalaxone. From the premix plate 50 μL was transferred to an assay plate containing the membranes, in duplicate. The assay plate was incubated for 2 h at room temperature. A GF/C 96 well filter plate (Perkin Elmer #6005174) was pretreated with 0.3% polyethylenimine for 30 min. The contents of the assay plate were filtered through the filter plate using a Packard Filtermate Harvester, and washed 3 times with 0.9% saline at 4° C. The filter plate was dried, underside sealed, and 30 μL Microscint 20 (Packard #6013621) was added to each well. A Topcount-NXT Microplate Scintillation Counter (Packard) was used to measure emitted energies in the range of 2.9 to 35 KeV. Results were compared to maximum binding, wells receiving no inhibitions. Nonspecific binding was determined in presence of 50 μM unlabeled naloxone. The biological activity of the dimer is shown in FIG. 3.

Results: The graphs in FIG. 3 show that the dimer has significant affinity for the opioid μ receptor The opioid μ receptor affinity of the buprenorphine dimer at 10-8M (~10 ng) and the profile is similar to that of buprenorphine.

B. Human κ Opioid Receptor Binding Assay

Figure 4:
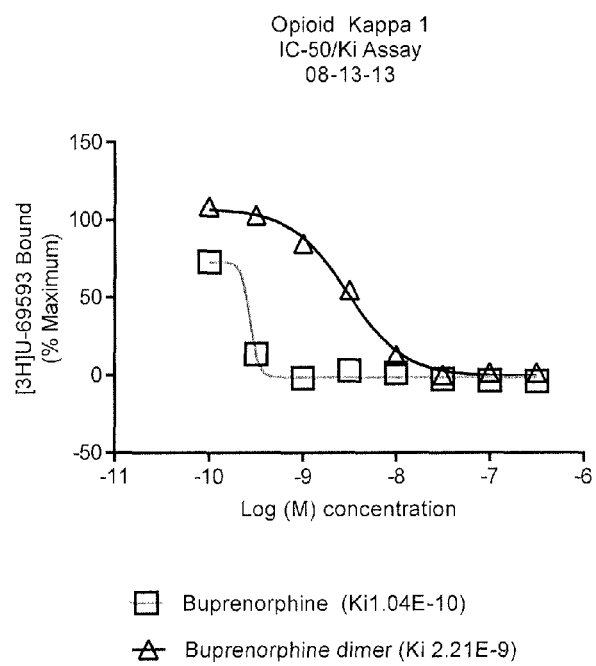
FIG. 4 provides the results of buprenorphine dimer receptor binding experiments—κ receptor.

Membranes from cloned HEK-293 cells expressing the human kappa opioid receptor (Amersham Biosciences UK Ltd. 6110558 200U) were homogenized in assay buffer (50 mM Tris, pH 7.5 with 5 mM MgCl2) using glass tissue grinder, Teflon pestle and Steadfast Stirrer (Fisher Scientific). The concentrates of the membranes were adjusted to 300 μg/mL in assay plate, a 96 well round bottom polypropylene plate. The compound to be tested was solubilized in DMSO (Pierce), 10 mM, then diluted in assay buffer to 3.6 nM. In a second 96 well round bottom polypropylene plate, known as the premix plate, 60 μL of 6× compound was combined with 60 μL of 3.6 nM 3H-Diprenorphine (DPN). From the premix plate, 50 μL was transferred to an assay plate containing the membranes, in duplicate. The assay plate was incubated for 18 h at room temperature. A GF/C 96 well filter plate (Perkin Elmer #6005174) was pretreated with 0.3% polyethylenimine for 30 min. The contents of the assay plate were filtered through the filter plate using a Packard Filtermate Harvester, and washed 3 times with 0.9% saline at 4° C. The filter plate was dried, underside sealed, and 30 μL Microscint 20 (Packard #6013621) was added to each well. A Topcount-NXT Microplate Scintillation Counter (Packard) was used to measure emitted energies in the range of 2.9 to 35 KeV. Results were compared to maximum binding, wells receiving no inhibitions. Nonspecific binding was determined in presence of 50 μM unlabeled naloxone. The biological activity of the dimer is shown in FIG. 4.

Results: FIG. 4 describes the opioid κ receptor agonist profile of the buprenorphine monomer and the dimer. Neither the monomer nor the dimer of buprenorphine has lost its affinity for the κ receptor. Qualitatively, as with buprenorphine, the binding of the buprenorphine dimer to opioid κ receptor increases with concentration. It is estimated that at about 1 μg, the profile of the opioid κ receptor affinity of the dimer was similar to that of buprenorphine.

C. Human δ Opioid Receptor Binding Assay

The assay was designed to test the ability of a compound to interfere with the binding of tritiated naltrindole to the human δ subtype 2 opioid receptor. Membranes from Chinese Hamster Ovary cells expressing the human δ subtype 2 opioid receptor (Perkin Elmer #RBHODM400UA) were homogenized in assay buffer (50 mM Tris, pH 7.5 with 5 mM MgCl2) using a glass tissue grinder, Teflon pestle and Steadfast Stirrer (Fisher Scientific). The concentration of membranes was adjusted to 100 µg/mL in an assay plate, a 96 well round bottom polypropylene plate. The compound to be tested was solubilized in DMSO, 10 mM, then diluted in assay buffer to 6× the desired final concentration. The ligand, 3H-natrindole (Perkin Elmer #NET-1065) was also diluted in assay buffer to 6 nM. Aliquots of 3H-natrindole (50 µL) were transferred to the assay plate containing the membranes in duplicate. The assay plate was incubated for 30 minutes at room temperature. A GF/C 96 well filter plate (Perkin Elmer #6005174) was pretreated with 0.3% polyethylenimine for 30 min. The contents of the assay plate were filtered through the filter plate using a Packard Filtermate Harvester, and washed 3 times with 0.9% saline at 4° C. The filter plate was dried, the underside sealed, and a 30 µL MictoS=scint 20 (Packard #6013621) added to each well. A Topcount-NXT Microplate Scintillation Counter (Packard) was used to measure emitted energies in the range of 2.9 to 35 KeV. Results were compared to maximum binding, wells receiving no inhibitors. Nonspecific binding was determined in the presence of 1 µM unlabelled Natrindole. The biological activity of the buprenorphine dimer is shown in Table 2 below.

TABLE 2

| Compound | IC50 | Ki |
|---|---|---|
| Buprenorphine dimer | 7.6 nM | 2.87 nM |

Relative to the µ and κ opioid receptors, the dimer had poor affinity for the δ receptor.

Example 4

Receptor Stimulation Activity

This example illustrates the ability of the buprenorphine dimer compound provided herein to stimulate the µ-opioid receptor-mediated signaling.

µ Opioid Receptor Agonist and Antagonist Functional Assays: [35S]GTPγS Binding Assayin Chinese Hamster Ovaries expressing Human µ Receptors (CHO-hMOR) cell membranes.

Briefly, CHO-hMOR cell membranes were purchased from Receptor Biology Inc. (Baltimore Md.). About 10 mg/ml of membrane protein was suspended in 10 mM TRIS-HCl pH 7.2, 2 mM EDTA, 10% sucrose, and the suspension kept on ice. One mL of membranes was added to 15 mL cold binding assay buffer containing 50 mM HEPES, pH 7.6, 5 mM MgCl2, 100 mM NaCl, 1 mM DTT and 1 mM EDTA. The membrane suspension was homogenized with a polytron and centrifuged at 3000 rpm for 10 min. The supernatant was done centrifuged at 18,000 rpm for 20 min. The pellet was resuspended in 10 ml assay buffer with a polytron.

The membranes were pre-incubated with wheat germ agglutinin coated SPA beads (Amersham) at 25° C., for 45 min in the assay buffer. The SPA bead (5 mg/ml) coupled with membranes (10 µg/ml) were then incubated with 0.5 nM [35S]GTPγS in the assay buffer. The basal binding was that taking place in the absence of added test compound; this unmodulated binding was considered as 100%, with agonist stimulated binding rising to levels significantly above this value. A range of concentrations of receptor agonist SNC80 was used to stimulate [35S]GTPγS binding. Both basal and non-specific binding were tested in the absence of agonist; non-specific binding determination included 10 µM unlabeled GTPγS.

Buprenorphine dimer was tested for function as an antagonist by evaluating its potential to inhibit agonist-stimulated GTPγS binding using D-Phe-Cys-Tyr-D-Trp-Orn-Thr-Pen-Thr-NH2 (CTOP) as the standard. Radioactivity was quantified on a Packard Top Count. The following parameters were calculated:

% Stimulation=[(test compound cpm−non-specific cpm)/(basal cpm−non-specific cpm)]*100%
Inhibition=(% stimulation by 1 µM SNC80−% stimulation by 1 µM SNC80 in presence of test compound)*100/(% stimulation by 1 µM SNC80−100).

Figure 5:
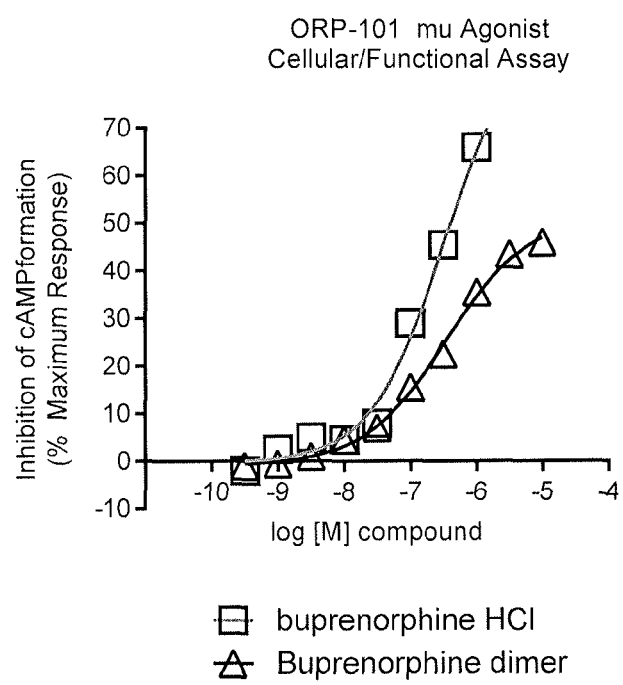
FIG. 5 provides μ, agonist functional assay results for the buprenorphine dimer.
Figure 6:
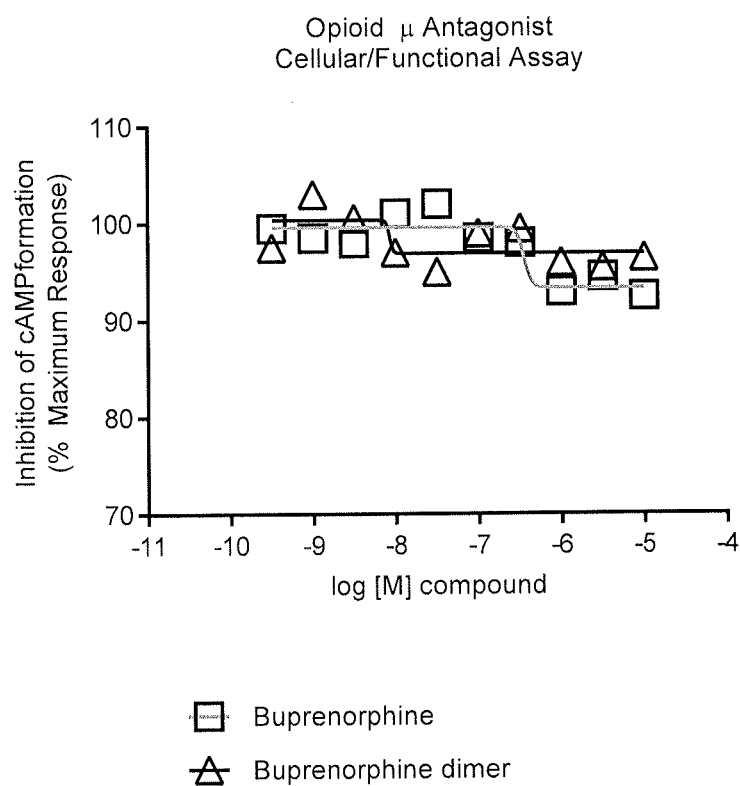
FIG. 6 provides μ antagonist functional assay results for the buprenorphine dimer.

EC50 was calculated using GraphPad Prism. A graph for the compound tested is shown in FIGS. 5 and 6.

Results: Data shown in FIG. 5 indicates that the dimer is a potent µ agonist. The results also indicate that the opioid µ receptor activity of the dimer at 10-6M (~1 µg) is similar to that of buprenorphine. Data in FIG. 6 shows that the dimer does not function as a µ-antagonist.

Example 5

Anti-Hyperalgesic Properties of the Dimer

A weak acetic acid solution administered rectally to neonatal mice results in colonic hypersensitivity when the mice reach maturity, at 8-10 weeks of age. The resulting hyperalgesic condition is similar to that in irritable bowel syndrome (IBS) in humans, where hypersensitivity, and resulting hyperalgesia, is a major component of the disorder. This rodent hyperalgesia model has been validated in studies in mice and rats.

In this study, neonatal mice were given a rectal infusion of 20 ul of 0.5% acetic acid or saline at 10 days after birth. After reaching adulthood (8-10 weeks of age), a pair of electrodes was placed in the abdominal external oblique muscle, 5-10 days before the test.

On the testing day, a wire was connected to the electrodes and a balloon catheter was inserted rectally under isoflurane anesthesia. Mice were then placed into a tube made from 50 ml syringe.

A visceral motor reflex (VMR) response to colonic rectal distention (CRD) was measured before any treatment (Baseline). Electromyographic (EMG) recordings were measured before (20 sec) and after application of pressure of 30 mmHg to the balloon for 10 sec.

The mice were then taken out of the tubes and gavaged with ORP-101 (50 mg/kg), or vehicle and were then placed back to the tube.

VMR responses to CRD (30 mmHg) were measured 30 and 60 minutes after the administration of ORP-101 or saline. Each measurement was repeated 2 times and the average response was calculated.

Figure 7:
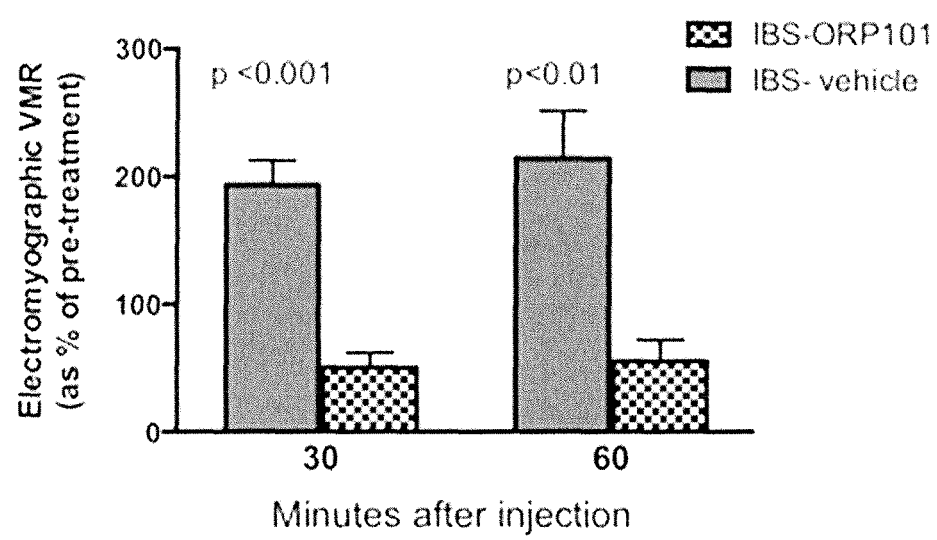
FIG. 7 provides the results of a demonstration in mice of the antihyperalgesic properties of the dimer.

The results are shown in FIG. 7, wherein the buprenorphine dimer is designated ORP-101. In mice receiving the dimer, colonic hypersensitivity and hyperalgesia were significantly reduced compared to the effect in mice receiving the saline control. This was demonstrated by a reduction in mouse abdominal external oblique muscle contractions in response to colonic pressure as measured by electromyography. The reduction in the VMR response was indicative of a reduction in colonic hypersensitivity and its resulting pain.

Example 6

Infusion Solution For Dilution With 0.9% Saline Solution

The composition of a vial of the infusion solution contains: a) 20 mg dimer base as the dihydrochloride salt, 400 mg PEG 300, 600 mg Polysorbate 80, 25 mg of soybean oil, and 5 mg of citric acid anhydrous.

Half of the PEG 300 and the citric acid are added to the temperature controlled mixing vessel, and the solution is mixed until the citric acid is dissolved. The drug is added to the solution, the remainder of the PEG300 is added, and the solution is mixed until the drug is dissolved. The polysorbate 80 and the soybean oil are added to the solution, and the final mixing of the solution occurs.

The solution is aseptically filtered and the vials are filled and capped under nitrogen.

Example 7

Subcutaneous Solution for Acute Treatment

ORP-101 diHCl salt equivalent to 1 g of free base is added to 1 L of sterile water for injection containing 50 g dextrose and mixed until fully dissolved. The 1 mg/mL drug base solution is sterile filtered and aseptically filled into clear glass vials and capped under nitrogen with caps that have no detectable leachables or extractables.

Example 8

In Situ Gelling Injectable for 1 Week

A liquid lipid stock solution is prepared by inverted mixing overnight containing soy phosphatidylcholine (PC) 40 g, glycerol monoleate (GMO) 40 g, ethanol 10 g, and tocopherol 0.3 g as an antioxidant. 10 g of the dimer as dihydrochloride salt is added to the stock solution and mixed. The solution is sterile filtered into glass vials capped with Teflon lined caps. The solution can be injected through a 21 gauge needle, and at body temperature in contact with water, it gels to form a viscous depot as the solvent disappears.

Example 9

In Situ Gelling Injectable for 1 Month 1 ml solution of PLGA polymer:N-methylpyrrolidone (70:30) is prepared with 100 mg of dimer compound dissolved. A gel forms when this solution is slowly dissolved into water, and the drug is slowly released over a period of 1 month.

It is understood that the examples and embodiments described herein are for illustrative purposes only and that various modifications or changes in light thereof will be suggested to persons skilled in the art and are to be included within the spirit and purview of this application and scope of the appended claims. To the extent there is conflict between the priority applications and the present application, any inconsistencies are to be resolved in favor of the present application. All publications and patents cited herein are hereby incorporated by reference in their entirety for all purposes.

What is claimed is:

1. A method of treating a patient suffering from peripheral neuropathic pain which comprises parenterally administering to said patient a therapeutically effective dose of a pharmaceutical composition comprising a pharmaceutically acceptable carrier or excipient and buprenorphine dimer compound having Formula (I):

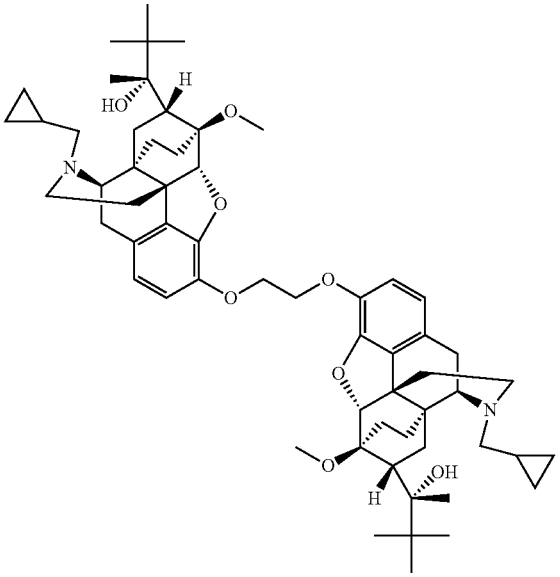

Formula (I)

or a pharmaceutically acceptable salt or solvate thereof.

2. The method according to method of claim 1, wherein the dimer compound is in the form of a pharmaceutically acceptable salt.

3. The method of claim 1 wherein the composition is administered intramuscularly or subcutaneously.

4. The method of claim 1 wherein the compound is administered by subcutaneous depot injection.

5. The method of claim 1, wherein the patient is a human and wherein the dose of dimer compound is administered is about 0.3 to about 1 mg.

6. The method of claim 4 wherein the dose of dimer compound is from about 5 to about 20 mgs.

7. The method of claim 4 wherein the dose of dimer compound is from about 20 to about 80 mgs.

8. The method of claim 4 wherein the patient suffered from diabetic neuropathic pain.

9. The method of claim 4 wherein the patient suffers from post herpetic neuropathic pain.

* * * * *